United States Patent [19]

Ikezaki et al.

[11] 4,032,575

[45] June 28, 1977

[54] BENZYLALCOHOL AMINE DERIVATIVES

[75] Inventors: Muneyoshi Ikezaki, Ageo; Nobuo Ito, Tokyo; Yasushi Okazaki, Tokyo; Masao Hoshiyama, Tokyo; Taku Nagao, Ageo; Hiromichi Nakajima, Yono, all of Japan

[73] Assignee: Tanabe Seiyaku Co., Ltd., Osaka, Japan

[22] Filed: Oct. 1, 1975

[21] Appl. No.: 618,355

[52] U.S. Cl. .................. 260/570.6; 260/343.7; 260/501.11; 260/501.12; 260/501.18; 260/501.19; 260/592; 424/280; 424/316; 424/330

[51] Int. Cl.² ........................ C07C 91/22

[58] Field of Search ............ 260/501.12, 501.18, 260/570.6; 424/316, 330

[56] References Cited

UNITED STATES PATENTS

| | | | |
|---|---|---|---|
| 3,255,249 | 6/1966 | Howe et al. | 260/570.6 X |
| 3,869,474 | 3/1975 | Miura et al. | 260/570.6 X |

OTHER PUBLICATIONS

Klosa, "Journal fur Praktiscke Chemie," vol. 36, pp. 1-4 (1967).
Burger, "Medicinal Chemistry," 2nd Ed., p. 597 (1960).
Thrift, "Jour. Chem. Soc. London," Series C, pp. 288-293 (1967).

Primary Examiner—Robert V. Hines
Attorney, Agent, or Firm—Bierman & Bierman

[57] ABSTRACT

A compound having the formula:

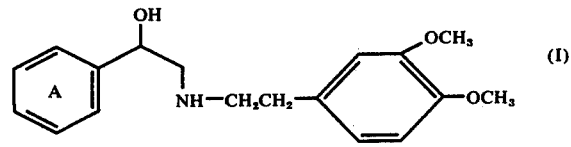

wherein Ring A is monohydroxyphenyl, or a pharmaceutically acceptable acid addition salt thereof is prepared by catalytic hydrogenation of a compound having the formula:

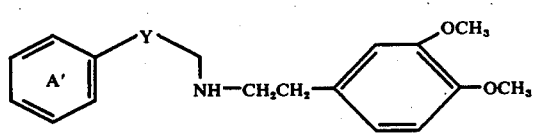

wherein A' is monobenzyloxyphenyl, and Y is carbonyl or hydroxymethylene. The compound (I) in which Ring A is 4-hydroxyphenyl or 3-hydroxyphenyl is useful as a cardiotonic agent. On the other hand, the compound (I) in which Ring A is 2-hydroxyphenyl is useful as an anti-diabetic agent.

3 Claims, No Drawings

BENZYLALCOHOL AMINE DERIVATIVES

This invention relates to a novel benzylalcohol derivative and a process for preparing same. More particularly, it relates to α-(3,4-dimethoxyphenethylaminomethyl)-monohydroxybenzylalcohol of the formula:

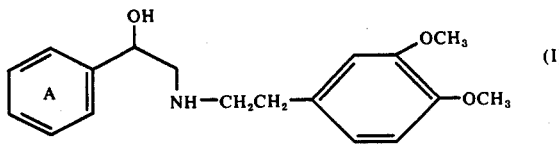

wherein Ring A is monohydroxyphenyl, or a pharmaceutically acceptable acid addition salt thereof.

The benzylalcohol derivative (I) in which Ring A is 4-hydroxyphenyl or 3-hydroxyphenyl has potent cardiac contractile activity and is useful as a cardiotonic agent without substantial side effects such as, for example, hypotensive activity. In particular, said benzylalcohol derivative is characterized by the high potency ratio of the adrenergic $\beta_1$-receptor stimulating activity (e.g., cardiac contractile and heart rate-increasing activities) to the adrenergic $\beta_2$-receptor stimulating activity (e.g., bronchodilating and hypotensive activities). For example, when α-(3,4-dimethoxyphenethylaminomethyl)- 4-hydroxybenzylalcohol of the invenion is injected into femoral vein of dogs at a dose of 8.0 μg/kg, said 4-hydroxybenzylalcohol derivative can increase the cardiac contractile force by 76%. Said 4-hydroxybenzylalcohol derivative also shows no influence upon blood pressure at a dose of 5.0 μg/kg which is necessary to increase the cardiac contractile force by 50%. Further, when α-(3,4-dimethoxyphenethylaminomethyl)-3-hydroxybenzylalcohol is injected into femoral vein of dogs at a dose of 10 μg/kg, said 3-hydroxybenzylalcohol derivative can increase the cardiac contractile force by 55% without substantial influence upon the blood pressure. Miura, Ikezaki et al. disclose that α-(3,4,5-trimethoxyphenethylaminomethyl)-3,4-dihydroxybenzylalcohol and α-(3,4-dimethoxyphenethylaminomethyl)-3,4dihydroxybenzylalcohol show selective activation of adrenergic $\beta_1$-receptor (U.S. Pat. No. 3,869,474 and Offenlegungsschrift 2,420,427). As compared with these known compounds, the 4- or 3-hydroxybenzylalcohol derivative (I) of the present invention shows stronger cardiac contractile and heart rate-increasing activities for a longer period of time by the oral administration thereof. When administered directly into digestive tracts (e.g., the duodenum) of dogs, for example, α-(3,4-dimethoxyphenethylaminomethyl)-4-hydroxybenzylalcohol shows the cardiac contractile activity for about 2 times longer period of time as compared with α-(3,4-dimethoxyphenethylaminomethyl)-3,4-dihydroxybenzylalcohol, and the heart rate-increasing activity for about 2 times longer period of time as compared with α-(3,4,5-trimethoxyphenethylaminomethyl)-3,4-dihydroxybenzylalcohol.

The benzylalcohol derivative (I) in which Ring A is 2-hydroxyphenyl has no substantial cardiac contractile activity. However, said 2-hydroxybenzylalcohol derivative of the invention can induce remarkable decrease of blood sugar and is useful as an anti-diabetic agent. For example, when α-(3,4-dimethoxyphenethylaminomethyl)-2-hydroxybenzylalcohol is administered orally to mice at a dose of 10 mg/kg prior to subcutaneous injection of glucose (one g/kg), said 2-hydroxybenzylalcohol derivative of the invention decreases the blood sugar level by about 30%. On the other hand, when examined under the same conditions as above, 100 mg/kg of Phenformin (Chemical name: 1-phenethylbiguanide) are required to induce 13% decrease in said blood sugar.

Further, the toxicity of the benzylalcohol derivative (I) of the present invention is remarkably low. For example, the 50% lethal dose ($LD_{50}$) of α-(3,4-dimethoxyphenethylaminomethyl)-4-hydroxybenzylalcohol which is estimated by intravenous injection thereof to mice is about 198 mg/kg.

The benzylalcohol derivative (I) of the present invention can be used for pharmaceutical use either in the form of a racemic modification or in an optionally active form. The benzylalcohol derivative (I) can also be used for pharmaceutical use as the free base or a salt thereof. The base and salt thereof are readily convertible from one to the other by conventional manner. Pharmaceutically acceptable salts are, for example, hydrochloride, hydrobromide, perchloride, nitrate, sulfate, phosphate, acetate, propionate, glycollate, lactate, pyruvate, oxalate, ascorbate, hydroxymaleate, phenylacetate, aminobenzoate, methanesulfonate, malonate, succinate, maleate, fumarate, malate, citrate, tartrate, ethanesulfonate, benzenesulfonate, p-toluenesulfonate, sulfanilate, aspartate and glutamate. The benzylalcohol derivative (I) may be used in the form of a pharmaceutical preparation for enteral or parenteral administration. The benzylalcohol derivative (I) in which Ring A is 4-hydroxyphenyl or 3-hydroxyphenyl may be used for pharmaceutical use at a daily dose of one μg/kg to one mg/kg, especially 30 μg/kg to one mg/kg (for oral administration). On the other hand, the benzylalcohol derivative (I) in which Ring A is 2-hydroxyphenyl may be used at a daily dose of 20 μg/kg to 2 mg/kg. Moreover, the benzylalcohol derivative (I) of the present invention may be used in conjunction or admixture with a pharmaceutical excipient that is suitable for enteral or parenteral administration. The excipient selected should be the one that does not react with the benzylalcohol derivative (I). Suitable excipients include, for example, gelatin, lactose, glucose, sodium chloride, starch, magnesium stearate, talcum, vegetable oil and benzylalcohol. Other known medicinal excipients may be employed. The pharmaceutical preparation may be a solid dosage form such as a tablet, a coated tablet, a pill or a capsule, or a liquid dosage form such as a solution, a suspension or an emulsion. The pharmaceutical preparation may be sterilized and/or may contain auxiliaries such as preserving, stabilizing, wetting or emulsifying agents.

According to the present invention, the benzylalcohol derivative (I) can be prepared by the steps of condensing a α-halo-monobenzyloxyacetophenone (II) with 3,4-dimethoxyphenethylamine to give a α-(3,4-dimethoxyphenethylamino)-monobenzyloxyacetophenone (III), optionally reducing the compound (III) to give a α-(3,4-dimethoxyphenethylaminomethyl)-monobenzyloxybenzylalcohol (IV), and then subjecting the compound (III) or (IV) to catalytic hydrogenation.

The above-mentioned reactions are shown by the following scheme:

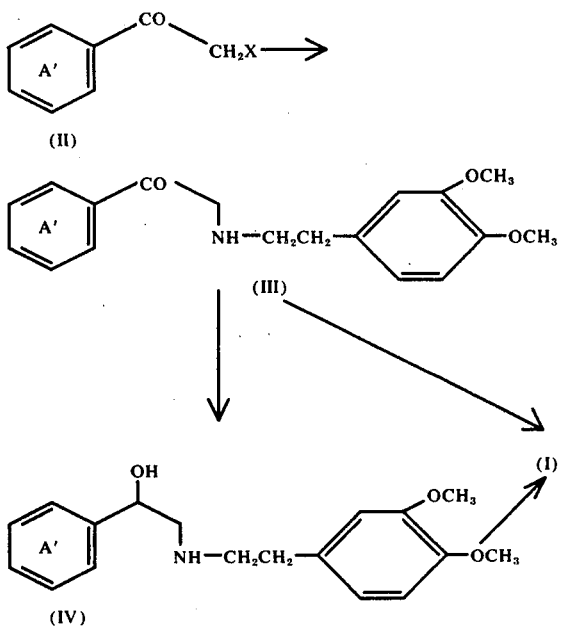

wherein Ring A' is monobenzyloxyphenyl and X is halogen.

The starting compound (II) is readily obtainable. For example, said compound may be prepared by dropwise addition of sulfuryl halide (e.g., sulfuryl chloride, sulfuryl bromide) to a methylene chloride solution of a monobenzyloxyacetophenone at 0° to 30° C under stirring.

The condensation of the α-halo-monobenzyloxyacetophenone (II) with 3,4-dimethoxyphenethylamine can be accomplished in a conventional manner. For example, the compound (III) is prepared by admixing the compound (II) with 3,4-dimethoxyphenethylamine The condensation reaction is conducted with or without a solvent. The condensation reaction is also conducted in the presence or absence of an acid acceptor. It is preferred to carry out the reaction at a temperature of 20° to 50° C, especially 45° to 50° C. Preferred examples of the reaction solvent include methylene chloride, chloroform, tetrahydrofuran and a lower alkanol (e.g., methanol, ethanol, propanol). Alkali metal hydroxides (e.g., sodium hydroxide, potassium hydroxide), alkali metal carbonates (e. g., sodium hydroxide) and organic tertiary amines (e.g., trimethylamine, triethylamine, pyridine) are suitable as the acid acceptor.

The α-(3,4-dimethoxyphenethylamino)-monobenzyloxybenzylalcohol (IV) is prepared by reducing the resultant product (III) with an alkali metal borohydride or lithium aluminium hydride in a solvent. Lithium borohydride, potassium borohydride and sodium borohydride are employed as the alkali metal borohydride. When the alkali metal borohydride is employed for the reaction, a lower alkanol (e.g., methanol, ethanol, propanol, isopropanol) or a mixture of the lower alkanol and water is suitable as the reaction solvent. On the other hand, when lithium aluminium hydride is employed, tetrahydrofuran, ether and dioxane are suitable as the reaction solvent. It is preferred to carry out the reaction at a temperature of 0° to 50° C, especially 15° to 20° C.

The α-(3,4-dimethoxyphenethylamino)-monobenzyloxybenzylalcohol (IV) is always obtained in the form of a racemic modification and may be, if required, resolved into each of its optically active enantiomers. The optical resolution of the compound (IV) into each of its optically active enantiomers may be conducted by reacting the racemic modification of the compound (IV) with a resolving agent in a solvent to form the diastereoisomeric salts thereof, and separating the diastereoisomers into each components thereof by selective crystallization. By said selective crystallization, the least soluble diastereoisomer is recovered as crystals from the reaction mixture and the more soluble diastereoisomer remains in the reaction mixture. It is preferred to carry out the selective crystallization at a temperature of 0° to 10° C. Ptosylphenylalanine, D-acetyl-phenylalanine, d-camphorsulfonic acid, d-α-bromocamphorsulfonic acid, malic acid, tartaric acid and their derivatives may be used as the resolving agent. The solvent which is employed in this resolution procedure should be the one in which the solubilities of the two diastereoisomers are sufficiently different from each other. For this purpose it is suitable to use water, a lower alkanol (e.g., methanol, ethanol, propanol), ethyl acetate, chloroform or a mixture of these solvents.

The α-(3,4-dimethoxyphenethylamino)-monobenzyloxyacetophenone (III) or α-(3,4-dimethoxyphenethylaminomethyl)-monobenzyloxybenzylalcohol (IV) is then subjected to catalytic hydrogenation to give the α-(3,4-dimethoxyphenethylaminomethyl)-monohydroxybenzylalcohol (I). Said catalytic hydrogenation is carried out by shaking a solution of the compound (III) or (IV) in the presence of a catalyst in a hydrogen atmosphere. Preferred examples of the catalyst include platinum dioxide, platinum and palladium-carbon. A lower alkanol (e.g., methanol, ethanol, propanol, isopropanol) or a mixture of the lower alkanol and water is suitable as the reaction solvent. It is preferred to carry out the reaction at 5° to 20° C under atmospheric pressure.

Practical and presently-preferred embodiments of the present invention are illustratively shown in the following Examples.

EXAMPLE 1 a. A solution of 3.9 g of α-chloro-4-benzyloxyacetophenone in 100 ml of methylene chloride is added dropwise to 8.2 g of 3,4-dimethoxyphenethylamine at room temperature. The mixture is heated at 50° C for 15 minutes. After cooling, 50 ml of methylene chloride are added to the mixture, and said mixture is washed with 20 ml of 10% hydrochloric acid and water. Then, the mixture is dried and evaporated to remove solvent. The viscous oil thus obtained is recrystallized from isopropanol. 3.95 g of α-(3,4-dimethoxyphenethylamino)-4-benzyloxyacetophenone hydrochloride are thereby obtained. M.p. 193° – 198° C.

b. 2.21 g of α-(3,4-dimethoxyphenethylamino)-4-benzyloxyacetophenone hydrochloride are suspended in 70 ml of ethanol, and 1.1 g of sodium borohydride are added thereto. The suspension is stirred at room temperature for 1.5 hours. Then, the suspension is evaporated to remove solvent. 5 ml of water are added to the residue, and the aqueous mixture is extracted with 50 ml of methylene chloride. The extract is washed with water, dried and evaporated to remove solvent. The oily residue thus obtained is treated with 9% hydrochloric acid in usual manner and then recrystallized from a mixture of ethanol and isopropylether.

1.96 g of α-(3,4-dimethoxyphenethylaminomethyl)-4-benzyloxybenzylalcohol hydrochloride are thereby obtained. M.p. 168° – 170° C.

c. A mixture of 0.62 g of α-(3,4-dimethoxyphenethylaminomethyl)-4-benzyloxybenzylalcohol hydrochloride, 0.2 g of 10% palladium-carbon and 200 ml of isopropanol is shaken at room temperature in hydrogen gas under atmospheric pressure. After hydrogen uptake is completed, the mixture is filtered to remove the catalyst. Then, the filtrate is concentrated to dryness, and the residue obtained is recrystallized from a mixture of isopropanol and isopropylether. 0.42 g of α-(3,4-dimethoxyphenethylaminomethyl)-4-hydroxybenzylalcohol hydrochloride is thereby obtained. M.p. 164° – 167° C.

EXAMPLE 2 a. α-(3,4-dimethoxyphenethylaminomethyl)-4benzyloxybenzylalcohol is prepared in the same manner as described in Example 1-(b). 4.7 g of α-(3,4-dimethoxyphenethylaminomethyl)-4-benzyloxybenzylalcohol and 2.25 g of (−)-D-acetylphenylalanine are dissolved in 150 ml of ethanol. Then, the solution is allowed to stand at about 5° C for 24 hours. Crystalline precipitates are collected by filtration, and the precipitates are recrystallized from ethanol. 2.19 g of l-α-(3,4-dimethoxyphenethylaminomethyl)-4-benzyloxybenzylalcohol (−)-D-acetylphenylalanine salt are obtained. M.p. 156°–158° C. $[\alpha]_D^{27}$ −44.6°(C = 0.74, methanol) Free base (recrystallized from ethyl acetate): M.p. 109° – 110° C. $[\alpha]_D^{28}$ −22.9°(C = 0.72, methylene chloride) Hydrochloride(recrystallized from ethanol): M.p. 175° – 177° C. $[\alpha]_D^{28}$ −23.2°(C = 0.74, methanol)

b. 2.89 g of l-α-(3,4-dimethoxyphenethylaminomethyl)-4-benzyloxybenzylalcohol hydrochloride, 1.0 g of 10% palladium-carbon and 150 ml of isopropanol are treated in the same manner as described in Example 1-(c). 1.35 g of l-α-(3,4-dimethoxyphenethylaminomethyl)-4-hydroxybenzylalcohol hydrochloride are obtained. M.p. 138° – 139.5° C(recrystallized from isopropanol).

EXAMPLE 3

4.45 g of α-(3,4-dimethoxyphenethylamino)-4-benzyloxyacetophenone hydrochloride prepared in the same manner as described in Example 1-(a) are dissolved in 600 ml of 80% aqueous isopropanol, and 0.70 g of platinum dioxide is added thereto. The mixture is shaken at room temperature in hydrogen gas under atmospheric pressure. After hydrogen uptake is completed, the mixture is filtered to remove the catalyst. Then, the filtrate is concentrated to dryness. 1.70 g of α-(3,4-dimethoxyphenethylaminomethyl)-4-hydroxybenzylalcohol hydrochloride are thereby obtained. The physicochemical properties of this product are identical with those of the compound obtained in Example 1.

EXAMPLE 4 a. A solution of 5.2 g of α-chloro-3-benzyloxyacetophenone in 30 ml of methylene chloride is added dropwise to 11 g of 3,4-dimethoxyphenethylamine. The mixture is heated at 50° C for 15 minutes. Then, the mixture is treated in the same manner as described in Example 1-(a). 5.7 g of α-(3,4-dimethoxyphenethylamino)-3-benzyloxyacetophenone hydrochloride are obtained. M.p. 195° – 198° C(recrystallized from methanol).

b. 2.78 g of α-(3,4-dimethoxyphenethylamino)-3-benzyloxyacetophenone hydrochloride, 0.76 g of sodium borohydride and 100 ml of ethanol are treated in the same manner as described in Example 1-(b). 2.73 g of α-(3,4-dimethoxyphenethylaminomethyl)-3-benzyloxybenzylalcohol hydrochloride are obtained. M.p. 127°–131° C(recrystallized from a mixture of isopropanol and ether).

c. 2 g of α-(3,4-dimethoxyphenethylaminomethyl)-3-benzyloxybenzylalcohol hydrochloride, 0.5 g of 10% of palladium-carbon, 100 ml of isopropanol and 15 ml of water are treated in the same manner as described in Example 1-(c). 1.45 g of α-(3,4dimethoxyphenethylaminomethyl)-3-hydroxybenzylalcohol hydrochloride are obtained. M.p. 161° –162° C(recrystallized from a mixture of isopropanol and ether).

EXAMPLE 5 a. A solution of 5 g of α-chloro-2-benzyloxyacetophenone in 15 ml of methylene chloride is added dropwise to 10.5 g of 3,4-dimethoxyphenethylamine. The mixture is refluxed for one hour. Then, the mixture is treated in the same manner as described in Example 1-(a). 4 g of α-(3,4-dimethoxyphenethylamino)-2-benzyloxyacetophenone hydrochloride are obtained. M.p. 177° – 180° C(recrystallized from ethanol).

b. 3 g of α-(3,4-dimethoxyphenethylamino)-2-benzyloxyacetophenone hydrochloride, 0.7 g of sodium borohydride and 30 ml of ethanol are treated in the same manner as described in Example 1-(b). 2.5 g of α-(3,4-dimethoxyphenethylaminomethyl)-2-benzyloxybenzylalcohol hydrochloride are obtained. M.P. 115° – 117° C(recrystallized from a mixture of ethanol and ether).

c. One g of α-(3,4-dimethoxyphenethylaminomethyl)-2-benzyloxybenzylalcohol hydrochloride, 0.3 g of 10% palladium-carbon and 30 ml of 80% aqueous isopropanol are treated in the same manner as described in Example 1(c). 0.75 g of α-(3,4-dimethoxyphenethylaminomethyl)-2-hydroxybenzylalcohol hydrochloride are obtained. M.p. 141° – 143° C(decomp.)(recrystallized from a mixture of ethanol and ether). ½ Oxalate: M.p. 175° – 176° C(recrystallized from ethanol).

What we claim is:
1. A compound of the formula:

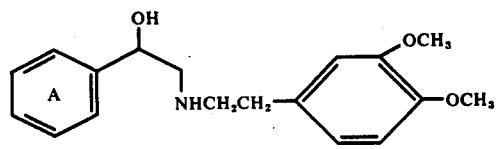

wherein Ring A is 4-hydroxyphenyl or a pharmaceutically acceptable acid addition salt thereof.

2. A compound of the formula:

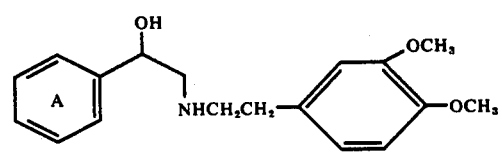

wherein Ring A is 2-hydroxyphenyl or a pharmaceutically acceptable acid addition salt thereof.

3. l-α-(3,4-dimethoxyphenethylaminomethyl)-4-hydroxybenzylalcohol or a pharmaceutically acceptable acid addition salt thereof.

* * * * *